United States Patent [19]
Raines et al.

[11] Patent Number: 5,566,677
[45] Date of Patent: Oct. 22, 1996

[54] CALIBRATION OF SEGMENTAL BLOOD CHANGES IN ARTERIES AND VEINS DURING DETECTION OF ATHEROSCLEROSIS

[76] Inventors: Jeffrey K. Raines, 770 Claughton Island Dr. No. 402, Miami, Fla. 33131; Leon T. Snyder, 1461 SW. 16th St., Boca Raton, Fla. 33486; John Hoffman, 5646 Old Fort Jupiter Rd., Jupiter, Fla. 33458

[21] Appl. No.: 285,904

[22] Filed: Aug. 4, 1994

[51] Int. Cl.$^6$ ............................................. A61B 5/02
[52] U.S. Cl. ............................................. 128/694
[58] Field of Search .................. 128/668, 672, 128/691, 692, 693, 694, 734

[56] References Cited

U.S. PATENT DOCUMENTS

| | | | |
|---|---|---|---|
| 4,144,878 | 3/1979 | Wheeler | 128/2.05 |
| 4,432,374 | 2/1984 | Osanai | 128/694 |
| 5,241,963 | 9/1993 | Shankar | 128/668 |
| 5,297,556 | 3/1994 | Shankar | 128/668 |
| 5,343,867 | 9/1994 | Shankar | 128/668 |

*Primary Examiner*—Angela D. Sykes
*Assistant Examiner*—Eric F. Winakur
*Attorney, Agent, or Firm*—Robert C. Kain, Jr.

[57] ABSTRACT

The method of calibrating includes selecting discrete levels of cuff pressure and placing the artery or vein under study under discrete levels of induced pressure with a closed pneumatic system contained by the pressure cuff, substantially continually sensing cuff pressures at each discrete level and thereby sensing blood volume change through the artery, electronically determining when a certain number of representative time-based blood volume change signals are substantially equivalent, changing the volume in the closed pneumatic system at each discrete cuff pressure by a pre-determined volumetric amount after determining substantial equivalency, electronically generating a calibration signal at each discrete cuff pressure based upon the calibrated volume change and, correcting the blood volume representative signal based upon the calibration signal at each discrete level of pressure. The calibration device includes, in one embodiment, a controllable pneumatic pump, a pressure sensor, a computerized device for determining when a representative number of blood volume change signals (based on the pressure sensor signals) are substantially similar and thereafter generating a calibration signal. The calibration system also includes a device which changes the volume in the closed pneumatic system by a pre-determined calibrated amount in the presence of the calibration trigger signal. This volume changing device may be a series of valves coupled by a chamber having a known volumetric size or a positive displacement pump driven by a stepper motor. The calibration system also includes a computerized device for correcting representative blood volume change signals based on the pressure signals at each discrete level of cuff pressure as corrected by the calibration signals represented by detected pressure signals obtained substantially simultaneously with the change of the volume at each discrete level of cuff pressure.

8 Claims, 5 Drawing Sheets

CALIBRATION OF SEGMENTAL BLOOD CHANGES IN ARTERIES AND VEINS DURING DETECTION OF ATHEROSCLEROSIS

BACKGROUND OF THE INVENTION

The present invention relates to a method and an apparatus for the calibration of segmental volume changes through arteries and veins during detection of atherosclerosis.

U.S. Pat. Nos. 5,241,963 to Shankar and 5,297,556 to Shankar disclose a method of detecting the onset and relative degree of atherosclerosis in humans and a method of detecting atherosclerosis while excluding motion artifacts. The Shankar disclosures discuss a volume plethysmograph which, in one embodiment, obtains a waveform which represents arterial blood volume change or segmental volume changes through an artery and compares that volume change signals measured at a plurality of discrete cuff pressure levels. The Shankar volume plethysmograph included a valve and a pump which was used to establish the discrete levels of pressure in a pressure cuff. A pressure transducer generated pressure signals based upon the change in pressure developed by pulsatile blood flow through the artery in the limb. This pulsatile blood flow is called segmental blood volume change herein. To calibrate the volume plethysmograph, the Shankar system first inflated the pressure cuff to a preset level and then injected a small amount of air into the pressure cuff by forcing air from a milled 1 ml chamber. The cuff was then fully deflated and the unit was calibrated electronically based upon the differential pressure signal (resulting in a differential blood volume signal) caused by the injection of the 1 ml volume of air injected to the closed pneumatic system. After the initial calibration and subsequent deflation, the pump was again activated to elevate the pressure in the cuff to a supra diastolic pressure (e.g., 70 mmHg) level. At this level, 1 ml of air was again injected into the cuff via an air chamber and the pressure sensor developed a signal that correlated to the 1 ml injection of air to that particular cuff pressure level. After this initial calibration at 70 mmHg, the volume plethysmograph then began inflating the cuff to pre-determined, discrete cuff pressure levels and measured the pressure change substantially continuously based upon the segmental blood volume change through the artery in the limb under study. The Shankar disclosures indicate that the automatic inflation and deflation, step deflation and calibration are performed by a peristaltic pump and a digital servo loop controlled microprocessor. The Shankar disclosure states "the 1 ml injection of air pressure by chamber 42 and electronic valve 40 into the cuff at any particular time can be utilized to further calibrate the signals." However, the Shankar disclosures also state that the 1 ml chamber cannot be precisely tooled or milled and the electromechanical coupling to the pneumatic system may cause a change from the 1 ml volume standard. Shankar states that "this tooling error and system error is accounted for by an initial calibration with a precise 1 ml reference. This initial calibration will lead to a multiplicative constant A that will change K to A delta $P_c$." The Shankar disclosures do not show, teach or suggest calibrating the measurement of segmental blood volume change through arteries at each discrete blood pressures as described in the present invention. This calibration at each discrete pressure level is necessary because the gain in the closed pneumatic system changes at each cuff pressure level.

In addition to a volume plethysmograph, the present invention can be utilized in conjunction with an oscillometric method of blood pressure measurement and in conjunction with pulse volume recording (PVR) devices.

U.S. Pat. No. 4,432,374 to Osanai discloses a volume plethysmograph. U.S. Pat. No. 4,144,878 to Wheeler discloses another impedance plethysmograph.

OBJECTS OF THE PRESENT INVENTION

It is an object of the present invention to provide a method and an apparatus to calibrate measurements of segmental blood volume change through arteries.

It is a further object of the present invention to provide a calibration method and device which calibrates blood volume signals at each discrete cuff pressure level.

It is another object of the present invention to provide a calibration system which first determines whether a series of time-based blood volume change signals are substantially equivalent and then generate a calibration trigger resulting in the change of volume of the closed pneumatic system.

It is a further object of the present invention to provide a calibration system which utilizes, in one embodiment, two (2) electrically activated valves.

It is another object of the present invention to provide a calibration system which utilizes, in another embodiment, a positive displacement pump driven by a stepper motor which is utilized to inject the calibration volume into the closed pneumatic system.

It is a further object of the present invention to incorporate the calibration method and device into a volume plethysmograph.

It is another object of the present invention to incorporate the calibration method and device into a device which detects the onset and the degree of atherosclerosis and the level of vascular compliance.

SUMMARY OF THE INVENTION

The method of calibrating includes selecting discrete levels of cuff pressure and placing the artery under study under discrete levels of induced pressure with a closed pneumatic system contained by the pressure cuff, substantially continually sensing cuff pressures at each discrete level and thereby sensing segmental blood volume change through the artery, electronically determining when a certain number of representative time-based blood volume change signals are substantially equivalent, changing the volume in the closed pneumatic system at each discrete cuff pressure by a pre-determined volumetric amount after determining substantial equivalency, electronically generating a calibration signal at each discrete cuff pressure based upon the calibrated volume change and, correcting the blood volume change representative signal based upon the calibration signal at each discrete level of pressure. The calibration device includes, in one embodiment, a controllable pneumatic pump, a pressure sensor, a computerized device for determining when a representative number of blood volume change signals (based on the pressure sensor signals) are substantially similar and thereafter generating a calibration signal. The calibration system also includes a device which changes the volume in the closed pneumatic system by a pre-determined calibrated amount in the presence of the calibration trigger signal. This volume changing device may be a series of valves coupled by a chamber having a known volumetric size or a positive displacement pump driven by a stepper motor. The calibration system also includes a computerized device for correcting or calibrating representative blood volume change signals based on the pressure signals at each discrete level of cuff pressure as corrected by the calibration signals represented by detected pressure signals obtained substantially simultaneously with the change of the volume at each discrete level of cuff pressure. The system corrects the acquired signal to obtain the correct blood volume change signal.

BRIEF DESCRIPTION OF THE DRAWINGS

Further objects and advantages of the present invention can be found in the detailed description of the preferred embodiments when taken in conjunction with the accompanying drawings in which.

DETAILED DESCRIPTION OF THE PREFERRED EMBODIMENTS

The present invention relates to a method and an apparatus for calibrating measurements of segmental blood volume changes through arteries and veins.

Figures 1, 2:
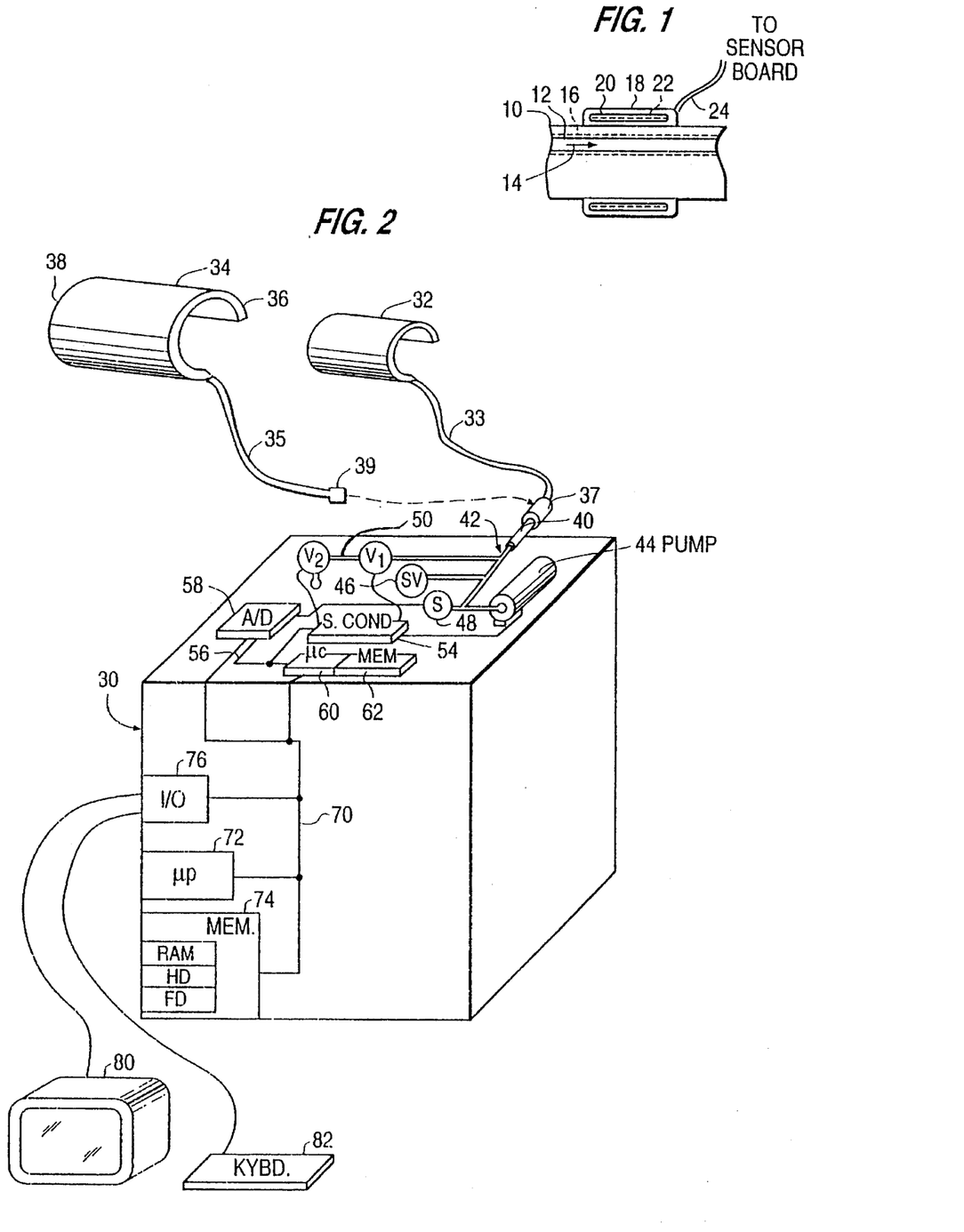
FIG. 1 diagrammatically illustrates a limb containing an artery under study and a blood pressure cuff surrounding the limb.
FIG. 2 diagrammatically illustrates various hardware components for the calibration method and device.

FIG. 1 diagrammatically illustrates, in cross section, a limb 10 of a patient (not shown) and an artery 12 contained within the limb. Blood flows through the artery in pulses in a direction illustrated by arrow 14 as an example in FIG. 1. Accordingly, artery 12 expands with each pulse or surge of blood as shown by dashed lines 16. This is called blood volume change or blood volume differential.

Bound about limb 10 is a pressure cuff 18 having, in its interior, a air bladder 20. When the blood pulses through artery 12, the limb expands and the pressure in the cuff changes and affects air bladder 20. The air bladder changes in size as shown by dashed lines 22. A closed pneumatic system is contained by pressure cuff 18 and particularly air bladder 20. Bladder 20 is in communication with a sensor board (discussed later) via coupler hose or tube 24.

FIG. 2 diagrammatically illustrates the hardware for one embodiment of the calibration device. In general, the calibration device is part of a computer system 30. In FIG. 2 two pressure cuffs 32 and 34 are illustrated. Pressure cuff 32 is generally a cylindrical pressure cuff that is commonly used on an arm or a calf. In contrast, cuff 34 is a conical cuff such that proximal end 36 has a smaller diameter as compared with distal end 38 when the conical cuff is placed about the thigh of a patient. These cuffs are known to persons of ordinary skill in the art.

Each cuff has a coupling hose 33 and 35 and a pneumatic attachable coupler 37, 39 which attaches to a port 40 on computer system 30. Port 40 leads to a pneumatic system generally illustrated by tubes, couplers, hoses or pipes 42 which are inside the container of computer system 30 (the container is not illustrated in FIG. 2).

Pneumatic internal coupling system 42 is connected to a pump 44, a valve $V_1$, a safety valve 46 (SV) and a pressure sensor 48 (S). Additionally, valve $V_1$ is pneumatically connected to a second valve $V_2$ via a closed chamber 50 having a pre-determined volume. As discussed in greater detail later, the pre-determined volume in chamber 50 is 1 ml. or 1 cc. Chamber 50 is a tube having an inside diameter of 4.5 mm and approximately 63 mm (2.48 inches) long. By maintaining valve $V_1$ closed while the cuff pressure in elevated to a predetermined level, (for example 70 mmHg), and then opening valve $V_1$ while maintaining valve $V_2$ closed, the volume in the closed pneumatic system (defined by substantially by the pressure cuff), is changed by a pre-determined volumetric amount. The electric signals precisely representing pressure generated by pressure sensor 48 during the pneumatic calibration routine provides a calibration signal which is used to calibrate the blood volume monitoring system.

FIG. 2 also diagrammatically illustrates the general electrical components and electrical system connections for the computer system. For example, valves $V_1$, $V_2$, pump 44 are all supplied with power (the power lines are not shown) and control signals. The control signals are generally sent from signal conditioner 54 to the valves and the pump. Signal conditioner 54 is coupled to an internal bus 56. This internal bus (on the pressure sensor board) also carries data and control signals to and from and analog/digital (A/D) device 58. A/D 58 is electrically connected to pressure sensor S 48 as shown in FIG. 2. Internal bus 56 is also connected to a micro controller 60 as well as a memory 62. Memory 62 may be a programmable read only memory (PROM) or other electronic device that stores computer programs. The code or micro code stored in memory 62 is utilized by micro controller 60 to drive, in conjunction with signal conditioner 54, valves $V_1$, $V_2$ and pump 44. Micro controller 60 also obtains, reviews and sends signals to and from A/D converter 58.

The output from A/D converter 58 is, as is known in the art, placed in a buffer and made available to other computer components via the main computer bus 70. This main computer bus is accessible by microprocessor 72, memory 74 and input/output device 76. Memory 74 includes a random access memory (RAM) a hard drive (HD) and a floppy or removable media drive (FD). It is important to note that the computer connects are only illustrated as an example herein. The device can be built in several ways with, for example, multiple busses, single memory devices, etc. Also, all electrical components shown in FIG. 1 are located in a lunch-box type personal computer container.

In one embodiment, pump 44 is manufactured by Seiko of Japan. The micro controller 60 is manufactured by Intel and is an 801186 micro controller. Microprocessor 72 is a 486-type microprocessor, the RAM holds 4 mega bytes of information and the hard drive has a reasonable size to store programs and waveforms and other patient data. Input/ output device 76 is electrically connected to a display monitor 80 and a keyboard 82. It should be noted that display monitor 80 may be incorporated within the container of computer system 30. These computers are typically called lunch-box type computer systems. Further, the entire computer system can be down sized significantly.

In a working embodiment, A/D converter 58 operates at approximately 250 samples per second to obtain digitized versions of the analog signals continually generated by the pressure sensor.

Figure 3:
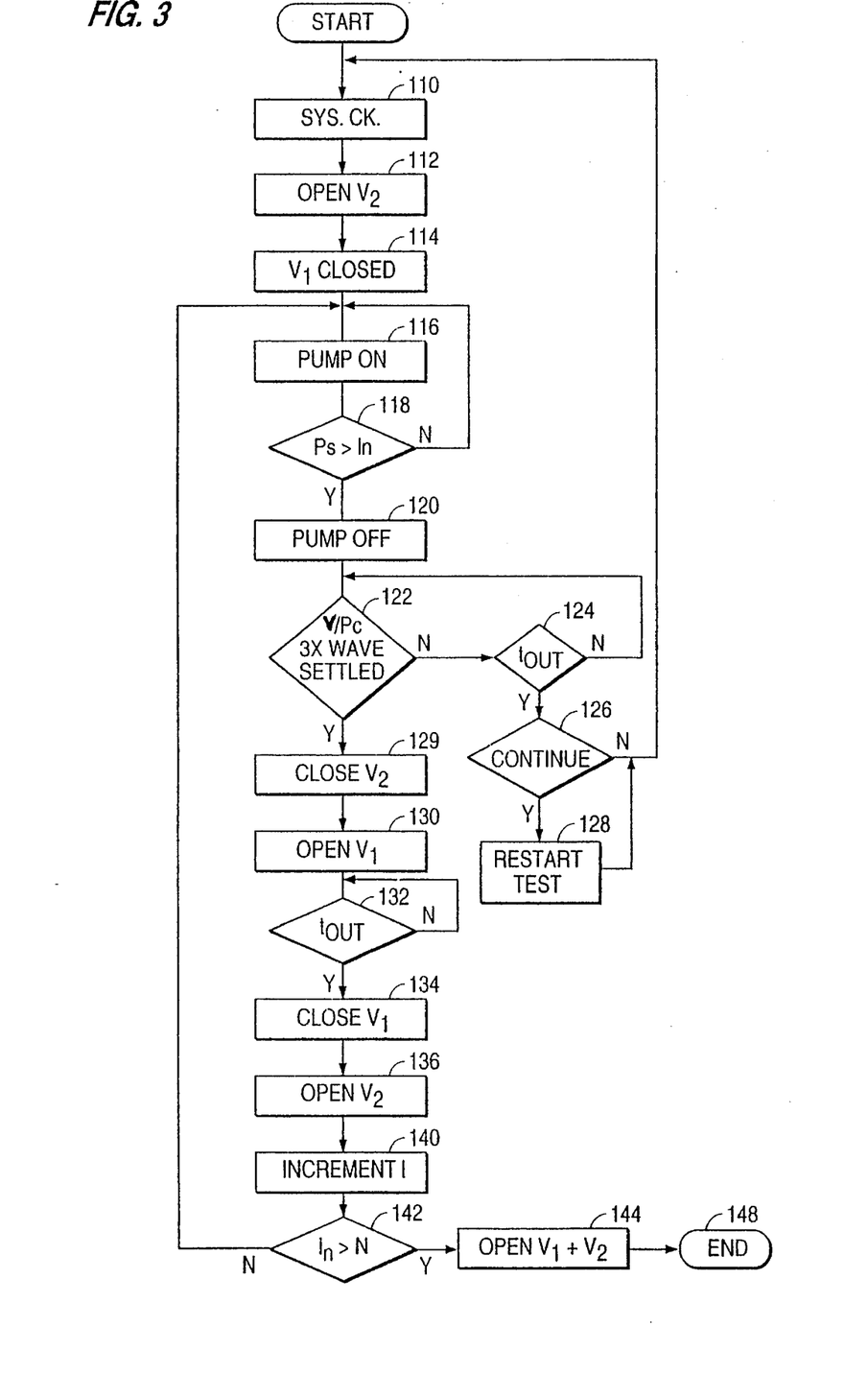
FIG. 3 diagrammatically illustrates the major elements of the flow chart which drives the valves in the calibration device and the calibration routine.

FIG. 3 diagrammatically illustrates the major elements of the flow chart or program routines utilized by the calibration system. In step 110, the computer system checks the various hardware components. In step 112, the system opens valve $V_2$. This vents any pressure in controlled calibration chamber 50 (FIG. 2) to the ambient environment. In step 114, valve $V_1$ is closed thereby creating a closed pneumatic system which includes pressure cuff 32, or 34, connector coupling 33, on board pneumatic coupling system 42, pump 44 and various valves such as valve $V_1$, safety valve SV and pressure sensor 48. Step 116 activates the pump which increases the air pressure in the system by a pre-determined amount. In one embodiment, this is 10 mmHg.

Decision step 118 determines whether the pressure in the closed pneumatic as sensed by pressure sensor 48 (FIG. 2) exceeds a first limit $1_n$. If not, the NO branch is taken and the program returns to a point immediately preceding step 116. If the YES branch is taken, the system turns off the pump in step 120. In decision step 122, the computerized system determines whether three blood volume change or pressure sensor time based signals are substantially equivalent. In other words, pressure sensor 48 substantially continually senses the pressure in the closed pneumatic system. These signals follow the pulsatile blood flow or blood volume change through the artery or vein. These sensed signals are converted from analog to digital by A/D converter 58 and are further processed by microprocessor 72 in conjunction with memory 74. The blood volume change signals or pressure sensor form signal waves. Once these signals or waves settle down into an acceptable, repetitive pattern as shown later in FIG. 4, the computer system and method can determine whether the pneumatic system defined by the pressure cuff and the artery under study has settled to an acceptable operational level or mode. If repetitive waveforms are not detected, the NO branch is taken and decision step 124 determines whether a time out clock has timed out. If the NO branch is taken from decision step 124, the system returns to a point immediately preceding decision step 122. If the YES branch is taken from time out step 124, the system has determined that it cannot locate and sense a repetitive number of n blood volume differential time-based representative signals which are similar. In one embodiment, n equal three (3).

Decision step 126 determines whether the system operator wants to continue the test. If not, the NO branch is taken and the program returns to a point immediately prior to system check step 110. If the system operator wants to continue, the YES branch is taken and step 128 restarts the test and returns the program to a point immediately preceding system check step 110.

Decision step 122 and the algorithms utilized to determine whether a sufficient number of pressure sensor and hence blood volume change waves are substantially equivalent is discussed later in conjunction with FIG. 4. If the computer system determined that small n number of waves are substantially similar, the YES branch is taken from decision step 122 and the system executes step 129 which closes valve $V_2$. In step 130, valve $V_1$ is opened. At this point, the closed pneumatic system generally contained within the blood pressure cuff has been altered by changing the volume by a pre-determined amount. In one working embodiment, this pre-determined amount is 1 ml. Again, pressure sensor 48 is continually generating signals showing the change in pressure in the closed pneumatic system during the calibration pulse. Decision step 132 determines whether a time out clock has expired. If not, the NO branch is taken and the system returns to a point immediately preceding decision step 132. If so, the YES branch and, in step 134, valve $V_1$ is closed. This valve isolates control volume calibration chamber 50 from the closed pneumatic system 42. In step 136, valve $V_2$ is opened thereby permitting equalization with atmospheric pressure in calibration chamber 50. In step 140, the system increments induced or cuff pressure level 1.

Decision step 142 determines whether the electronically set pressure level $1_n$ exceeds a maximum high pressure level N. If YES, the system, in step 144 opens both valves $V_1$ and $V_2$ and the program ends in step 148. If not, the NO branch is taken from step 142 and the system returns to a point immediately preceding pump on step 116.

Figure 4:
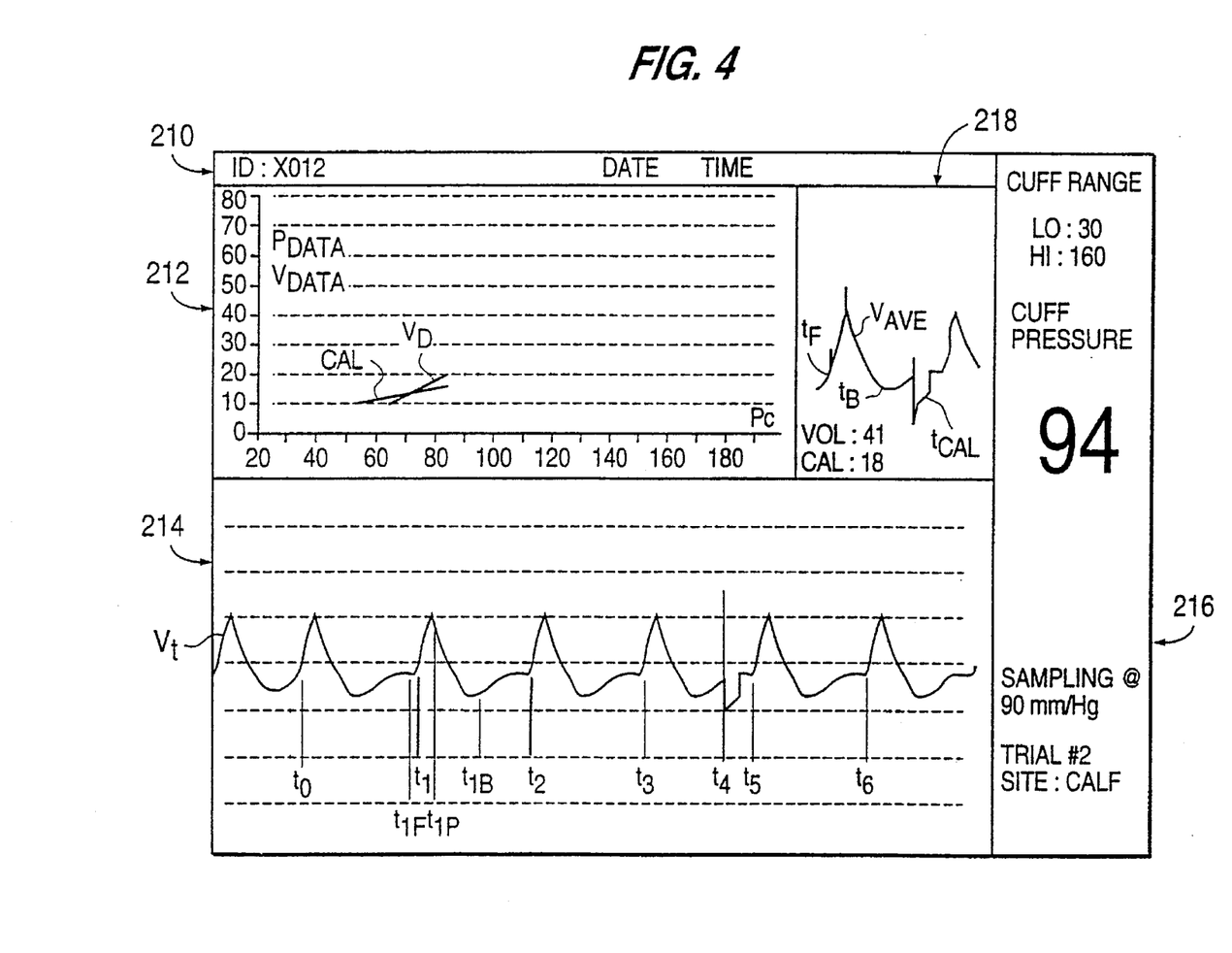
FIG. 4 diagrammatically illustrates both a display screen in accordance with the principles of the present invention as well as an annotated time-based signal which is representative of both the pressure sensor signal and, in a general sense, the time-based blood volume change signal (uncorrected)

FIG. 4 diagrammatically illustrates a display screen divided into five regions 210, 212, 214, 216 and 218. This display screen format may be visually presented on monitor 80 in FIG. 2 or on an incorporated screen as part of the container for computer system 30 (a lunch-box type computer system). In region 210, the patient's ID number or name, the date and time is displayed. In region 212, a substantially real time presentation of the pressure signal from pressure sensor 48 (FIG. 2) is shown as waveform portion $V_D$. As stated earlier, this pressure sensor signal also represents in a general sense, the blood volume change signal showing pulsatile blood flow through the artery.

Waveform portion or segment $V_D$ is initially obtained based upon the analog pressure signal developed by pressure sensor 48. This analog signal is converted into a digital signal in A/D converter 58. Processing of the continuous digital signal occurs with microprocessor 72 and memory 74. Further, A/D converter 58 is under the control of micro controller 60 and hence, some processing or analysis of the signal may be carried out by micro controller 60 as provided by programs in memory 62.

Returning to FIG. 4, display region 212 also includes another signal CAL which represents the calibration signal. An important feature of the present invention involves the calibration of the system at each discrete cuff pressure. For example, after one of the pressure cuffs 32, 34 is wrapped or bound about a limb containing the artery under study, that pressure cuff is inflated to a number of pre-determined discrete pressure levels. In a working embodiment, these pressure levels begin at a low pressure of 30 mmHg (sub-diastolic) and the cuff pressure is increased 10 mmHg increments while pressure sensor 48 substantially continually generates a pressure signal representative of changes in the cuff pressure. Accordingly, signals are obtained at 30 mmHg, 40 mmHg, 50 mmHg (the beginning of the calibration or CAL signal), at 60 mmHg and at 70 mmHg. The cuff pressure is incrementally increased 10 mmHg until a certain level is reached (supra-systolic) or until the cuff pressure exceeds 160 mmHg whichever is higher. The high cuff pressure level is set by the operator through an initialization program in the current embodiment.

Signals shown in display regions 212 $V_D$ and CAL are essentially raw or uncorrected signals. Signal $V_D$ is based upon the pressure signal sensed by pressure sensor 48. However, this signal is also representative of the blood volume change signal. This blood volume signal indicates the segmental blood volume change of blood flow through the artery (or vein) under study at each discrete cuff pressure level. Cuff pressures are identified in FIGS. 4, 5, and 6A–6D as signals $P_c$.

Display area 214 shows a plurality of waveforms which represent time-based pressure change signals. These time-based pressure signals, representative of segmental volume change signals are principally obtained from the output of pressure sensor 48. Signal $V_D$ and CAL shown in display region 212 not time-based signals. The Time Marker Table set forth below provides definitions for the time markers $t_0$–$t_6$. In the working embodiment, the time-based change signal illustrated in display region 214 does not include these annotations or time markers. These time marker annotations have been added in order to explain the operation of the present invention.

| Time Marker Table | |
|---|---|
| Time Marker | Description |
| $t_0$ | wave zero |
| $t_{1F}$ | leading foot wave code |
| $t_1$ | wave one leading edge |
| $t_{1P}$ | peak wave one |
| $t_{1B}$ | lagging base wave one |
| $t_2$ | wave two leading edge |
| . | |
| . | |
| . | |
| $t_4$ | leading edge calibration pulse |

Display region 216 illustrates the cuff pressure range beginning at a low pressure of 30 mmHg and a high pressure of 160 mmHg. Display region 216 also displays the current or real time cuff pressure "94" as well as the discrete cuff pressure target "sampling the @ 90 mmHg," the trial number and the site of the pressure cuff "calf." As explained above, the pressure cuff is bound about the thigh (a conical cuff 34) as well as, during a subsequent diagnostic procedure, the calf (a cylindrical pressure cuff 32).

Display region 218 diagrammatically illustrates the averaged segmental blood volume change waveform $V_{AVE}$. In the present embodiment, three repetitive waveforms are averaged.

Returning to the time-based blood pressure change signal $V_t$, the initial waveform is shown at time $t_0$. In one working embodiment, A/D converter samples the output of pressure sensor 48 approximately 250 times per second (250 Hertz). This sampling rate was selected in order to sense the leading edge of the volumetric calibration pulse. At this sampling rate and in view of common systolic and diastolic blood pressure levels and the low and high cuff pressure settings, microprocessor 72 and, in particular, memory 74 stores between 24 to 54 waveforms $V_t$.

Each pressure change waveform $V_t$ is identified, for purposes of discussion, as having a leading foot portion $t_{1F}$, a peak portion $t_{1P}$ and a lagging base portion $t_{1B}$. The waveforms in display region 214 are identified as $t_1$, $t_2$, $t_3$, $t_5$ and $t_6$.

Since the pressure sensor is substantially continually providing a signal representative of cuff pressure which is substantially representative of the blood volume change signal, and since the cuff pressure levels are elevated to known, discrete levels in the closed pneumatic system, it is necessary to permit the pneumatic system to settle down before acquiring the desired number n of blood volume change signals. In one working embodiment, the computer system determines when n number of representative time-based pressure change signals $V_t$ are substantially equivalent. This equivalency can be determined by many mathematical algorithms. The Waveform Trigger Table set forth below indicates one method.

WAVEFORM TRIGGER TABLE

- Does peak amplitude W1=W2=W3 within error % W1?
- Does 3rd derivative W1=W2=W3 and not zero within error a?
- Execute calibration $t_w$+ C
- Is $t_{w+1}$ wave similar to W1, W2 and W3
- Save+Average W1, W2, W3 aligned with selected wave feature One way to determine whether n number of time-based signals $V_t$ are substantially equivalent is to analyze whether the amplitude of each waveform W1 equals the amplitude of the next two peaks for waves 2 and 3 (does the amplitude of wave $t_1$ equal the amplitude of wave $t_2$ which in turn equals the amplitude of wave 13). Further, it may be necessary to insert an error range in this amplitude comparison. The amplitude is obtained by determining when the blood flow volume differential signal initially jumps or has a slope or a third derivative exceeding a certain pre-determined level. Another mathematical algorithm to determine when n number of waves are substantially equivalent is to monitor the third derivative of each waveform (an acceleration or jerk measurement). When this third derivative is not zero within an error range a, it is more likely than not that n number (3 in the present embodiment) of waves are substantially equivalent. There are other methods to determine substantial equivalency of the waves such as the area under the curve, the distance between the waveforms etc. The Wave Feature Table set forth below provides some aspects of the wave which may be monitored electronically be the computerized system.

WAVE FEATURE TABLE

Leading foot
Leading edge (1st, 2nd, 3rd derivative)
Peak
Lagging base

After the computerized system determines that n number of waves $V_t$ are substantially equivalent, the system generates a calibration trigger signal. This trigger signal is primarily generated by micro controller 60 and microprocessor 72. In other words, microprocessor 72 and memory 74 determine when n number of time-based pressure change signals $V_t$ are substantially equivalent, i.e., the pneumatic system has settled down. Thereafter, microprocessor 72 raises a flag or sends a control command to microcontroller 60. Microcontroller 60 then closes valve V2, opens valve V1 (the precise valve trigger signal) and, within a predetermined time period thereafter, closes valve $V_1$ and subsequently opens valve $V_2$ to vent the chamber.

Upon opening valve V1 (step 130 in FIG. 3), the closed pneumatic system primarily contained by pressure cuff 32, 34 experiences a change in volume by a predetermined amount. This predetermined amount is the interior size of the chamber defined by tube or cylinder 50. In one working embodiment, this chamber and predetermined amount is 1 ml. The 1 ml volume change results in a change in the pressure signal, thereby causing the calibration pulse as shown at time $t_4$ in signal $V_r$. The calibration pulse is delivered at each discrete cuff pressure level. Accordingly, at pressure levels 50, 60, 70, 80 . . . 160, the system will generate a calibration pulse and change the volume in the closed pneumatic system by a predetermined amount of 1 ml.

Figure 5:
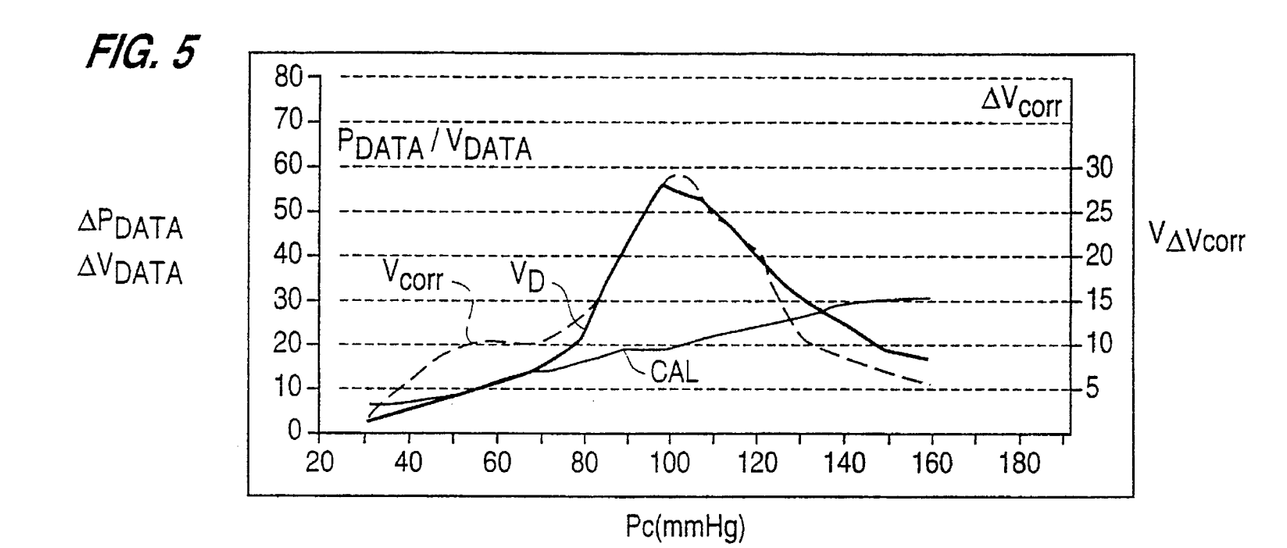
FIG. 5 diagrammatically illustrates a plot showing the calibration signal, the uncorrected blood volume change signal and the corrected blood volume change signal.

It has been found that the pneumatic gain of the closed pneumatic system changes dependent upon the cuff pressure. At higher cuff pressures, the system responds differently to pressure change signals and hence blood volume changes than at lower cuff pressures. This gain change feature is shown in FIG. 5 by viewing signal CAL. Equation 1 which follows generally represents the dynamics of the system.

$$V/P = V_{cc}/P_{cal} \qquad \text{Eq. 1}$$

where V is volume signal, P is pressure signal, $V_{cc}$ is volume of calibration chamber and $P_{cal}$ is sensed pressure change or differential at calibration pulse time.

Based on the foregoing, if $V_{cc}$ is equal to 1 ml, the sensed pressure change signal which is the drop at time $t_4$, can be used to calibrate the blood differential signal $V_D$ at each cuff pressure.

Accordingly, the sensed pressure signal $P_{data}$ is generally representative of the blood volume change signal $V_{data}$.

The calibration signal shown in FIG. 5 is the calibration signal sensed by pressure sensor 48 during each calibration pulse (see $t_4$ in FIG. 4). Using the calibration value and the uncorrected pressure change signal, the blood volume change signal $V_D$ can be corrected to obtain a corrected blood volume change signal $V_{corr}$ which is shown by dashed lines in FIG. 5.

The corrected blood volume change signal can be used with several devices, one of which is a volume plethysmograph. Other devices include pulse volume recorders. Further, the corrected blood volume change signal can be used to detect the onset and degree of atherosclerosis. Several devices to detect the onset and degree of atherosclerosis are described in U.S. Pat. No. 5,241,963 to Shankar entitled "Method for Detecting the Onset and Relative Degree of Atherosclerosis in Humans," issued Sep. 7, 1993. This U.S. patent to Shankar is incorporated herein by reference thereto.

Figure 6A:
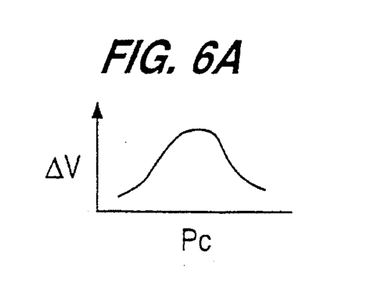
FIGS. 6A–6D diagrammatically illustrate plots showing different blood volume versus cuff pressure waveforms which progressively show the onset and the degree of atherosclerosis; and, FIG. 7 diagrammatically illustrates another hardware configuration for the calibration device.
Figure 6B:
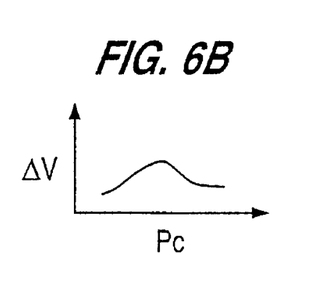
Figure 6C:
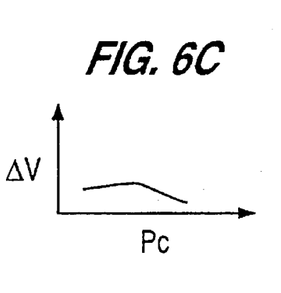
Figure 6D:
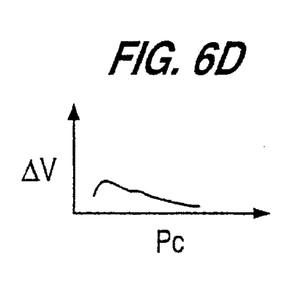

FIGS. 6A, 6B, 6C and 6D diagrammatically illustrate corrected blood volume change signals $\Delta V$ versus cuff pressure $P_c$ for arteries having increasing degrees of occlusion. In other words, the blood volume change versus discrete level of cuff pressure curve in FIG. 6A illustrates a generally healthy and compliant artery, the artery illustrated by the $\Delta V$ versus $P_c$ curve in FIG. 6B is more occluded, the artery under study shown in waveform $\Delta V$ versus $P_c$ in FIG. 6C is further occluded, and the artery illustrated in FIG. 6D is very occluded. As illustrated by the sequential FIGS. 6A–6D, the blood volume change versus cuff pressure waveform changes shape dependent upon the degree and onset of atherosclerosis. This is described in great detail in U.S. Pat. No. 5,241,963 to Shankar which is incorporated herein by reference thereto.

Returning to FIGS. 4 and 5, the computer system (FIG. 1) averages n number of blood volume change waves and displays them in display region 218. Preferably, this averaged wave is a corrected wave but may be an uncorrected averaged wave. The averaged wave is shown from point $t_F$ through $t_B$. The calibration pulse is shown beginning at $t_{cal}$. Of course, the calibration pulse is not averaged since the system is only calibrated once at each discrete cuff pressure. If the blood volume change wave shown in display region 218 is corrected, the calibration pulse $t_{cal}$ may not be illustrated. The corrected and averaged waveforms at each cuff pressure are saved in memory 74 for further processing. If the computerized system, primarily consisting of microprocessor 72 and memory 74, does not identify n number of representative time-based blood volume change signals being substantially equivalent, the system defaults, as shown in steps 124, 126 and 128 in FIG. 3 and restarts or quits.

It is important to note that the illustrations shown in FIGS. 4 and 5 are provided only as examples. The numbers for pressure data, volume data, and cuff pressures are simply illustrative and are not meant to be definitive. Further, the other information regarding the high and low pressure levels and the location of the items on the display screen is simply illustrative of one embodiment of the present invention.

The Waveform Trigger Table presented above also determines whether the wave following the trigger pulse, that is, the wave at time $t_5$ is substantially equivalent to the waves at $t_1$, $t_2$ and $t_3$. If so, then the system recognizes that the calibration pulse did not adversely affect the overall pneumatic response of the device. If no adverse effects or noise have been noted in the acquired signal, the system averages the waves $t_1$, $t_2$ and $t_3$ and saves them. This averaging is done by aligning these waves based upon a certain wave feature which may be the leading foot portion $t_f$, the leading edge $t_{\#}$, the first, second or third derivatives of the leading edge portion of the wave, the peak $t_P$ or the lagging base $t_B$.

Since a measurement of blood volume change is being accomplished by mechanically inflating a pressure cuff, the following Safety Systems Table may be incorporated in either the hardware, the routine stored in memory 62 or the routine stored in memory 64, or all.

SAFETY SYSTEMS TABLE

- If $P_{data} >$ P-MAX, then open $V_1$ and $V_2$
- If 3rd derivative $P_{data} > d^3$-P-MAX, then open $V_1$ and $V_2$
- Mechanical Safety Valve (SV) opens at P-MAX+ q The safety systems which may be incorporated in the present invention include continuously monitoring the pressure signal $P_{data}$ to determine whether that signal ever becomes greater than a high threshold P-max. If so, both valves $V_1$ and $V_2$ open. Alternatively, or in addition thereto, if the third derivative (an indicator of acceleration) of the pressure sensed signal $P_{data}$ becomes greater than the third derivative threshold $d^3$-P-max, then both valves $V_1$ and $V_2$ open. Further, the system should include a mechanical safety valve SV which opens whenever the pressure in the closed pneumatic exceeds a certain level which is selected as P-max plus a constant q.

Other safety systems may be included in the present invention.

The pump shown in FIG. 4 is a diaphragm pump which is manufactured by Seiko. The pressure sensor is manufactured by Motorola and is sold as model MPX2050, MPX2051, MPX2052. Rather than utilize a diaphragm pump, FIG. 7 illustrates the use of a positive displacement pump.

Figure 7:
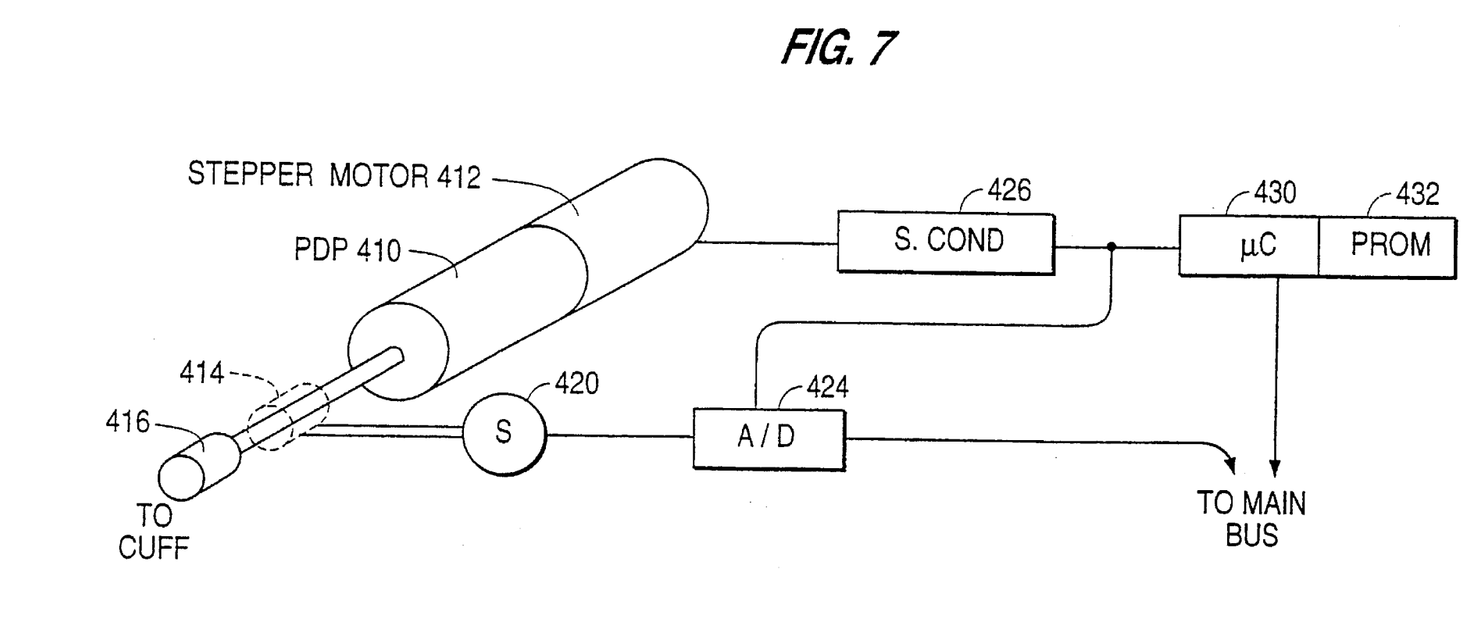

FIG. 7 diagrammatically illustrates another embodiment of the present invention using a positive displacement pump (PDP) 410 driven by a stepper motor 412. This pump may include a piston which, at each cycle, injects a known volume of air into the pneumatic system. The internal pneumatic coupling system 414 includes a mechanical coupler 416 which can be attached pressure cuffs 32, 34, and particularly coupler lines 39 and 37 shown in FIG. 2. Pressure sensor 420 is also pneumatically connected to the internal pneumatic line 414. A/D converter 424 obtains and converts the signal from pressure sensor S 420. Signal conditioner 426 generates signals to control the stepper motor which in turn controls the positive displacement pump. Microcontroller 430 and memory PROM 432 control the A/D converter 424 as well as the stepper motor 412.

In operation, the positive displacement pump injects a certain amount of fluid or air into the cuff pressure based upon the number of turns stepper motor 412 delivers to the pump drive. Accordingly, a stepper motor driven to a certain level (a certain number of rotations) can drive a positive displacement pump to a certain level and inject a predetermined amount of volume of air into the closed pneumatic system at each cuff pressure level. This injection of a calibration volume of air into the system is used to calibrate the pneumatic gain at each discrete cuff pressure level as explained earlier. Instead of evacuating 1 ml of air, the stepper motor and PDP pump inject 1 ml of air into the system.

We claim:

1. In combination with a volume plethysmograph which detects the degree of atherosclerosis by analysis of blood volume change at discrete levels of cuff pressure, an improved calibrated system for measuring blood volume changes through an artery of a patient with a pressure cuff bound about a limb containing said artery comprising:

a controllable pneumatic pump system for establishing a plurality of discrete levels of cuff pressure in said pressure cuff as a closed pneumatic system;

a pressure sensor substantially continually sensing and generating signals representative of cuff pressure and blood volume change through said artery at each one of said plurality of discrete levels of cuff pressure;

means for determining when a number of representative blood volume change signals are substantially similar at one of said plurality of discrete levels of cuff pressure and generating a calibration trigger signal;

means for changing a volume in said closed pneumatic system by a predetermined calibration amount based upon said calibration trigger signal;

means for generating a corrected representative blood volume signal based upon the representative cuff pressure signals each of said plurality of discrete levels of cuff pressure as corrected by representative cuff pressure signals obtained substantially simultaneously with the changing of said volume by said predetermined calibration amount;

wherein said pneumatic pump system includes a positive displacement pump driven by a motor, and said means for changing the volume by said predetermined calibration amount includes means for generating a drive signal to said pump such that said pump injects said predetermined calibration amount into said closed pneumatic system upon receipt of said calibration trigger signal.

2. A calibrated system as claimed in claim 1 wherein said means for changing the volume by said predetermined calibration amount includes a pneumatically closed chamber with a valve interposed between said chamber and said closed pneumatic system, said valve opened by said calibration trigger signal.

3. A calibrated system as claimed in claim 1 wherein said means for determining and said means for generating include a controllable processor and a memory.

4. In combination with a volume plethysmograph which detects the degree of atherosclerosis, the improvement which includes a calibrated system for measuring blood volume change through an artery of a patient with a pressure cuff bound about a limb containing said artery comprising:

a controllable pneumatic pump system for establishing a plurality of discrete levels of cuff pressure in said pressure cuff as a closed pneumatic system;

a pressure sensor substantially continually sensing and generating signals representative of instantaneous cuff pressure and blood volume change through said artery at each one of said plurality of discrete levels of cuff pressure;

means for determining when a number of representative blood volume change signals are substantially similar at one of said plurality of discrete levels of cuff pressure and generating a calibration trigger signal;

means for changing a volume in said closed pneumatic system by a predetermined calibration amount based upon said calibration trigger signal;

means for generating a corrected representative blood volume signal based upon the representative instantaneous cuff pressure signals at each of said plurality of discrete levels of cuff pressure as corrected by representative instantaneous cuff pressure signals obtained substantially simultaneously with the changing of said volume by said predetermined calibration amount;

wherein said pneumatic pump system includes a positive displacement pump driven by a motor, and said means for changing the volume by said predetermined calibration amount includes means for generating a drive signal to said pump such that said pump injects said predetermined calibration amount into said closed pneumatic system upon receipt of said calibration trigger signal.

5. In combination with a volume plethysmograph which detects the degree of atherosclerosis by analysis of blood volume change at discrete levels of cuff pressure, an improved calibrated system for measuring blood volume changes through an artery of a patient with a pressure cuff bound about a limb containing said artery comprising:

a controllable pneumatic pump system for establishing a plurality of discrete levels of cuff pressure in said pressure cuff as a closed pneumatic system;

a pressure sensor substantially continually sensing and generating signals representative of cuff pressure and blood volume change through said artery at each one of said plurality of discrete levels of cuff pressure;

means for determining when a number of representative blood volume change signals are substantially similar at one of said plurality of discrete levels of cuff pressure and generating a calibration trigger signal;

means for changing a volume in said closed pneumatic system by a predetermined calibration amount based upon said calibration trigger signal;

means for generating a corrected representative blood volume signal based upon the representative cuff pressure signals at each discrete level of cuff pressure as corrected by representative cuff pressure signals obtained substantially simultaneously with the changing of said volume by said predetermined calibration amount;

wherein said means for changing the volume by said predetermined calibration amount includes a first and a second valve and a pneumatically closed chamber with said first valve interposed between said chamber and said closed pneumatic system, said second valve in communication with said closed chamber and, when opened, providing a passage to an ambient environment, said first valve opened by said calibration trigger signal.

6. A calibrated system as claimed in claim 5 wherein said means for determining when said blood volume change signals are substantially similar and said means for changing the volume includes means for initially opening said second valve, closing said first valve, generating a first calibration signal when said blood volume change signals are substantially similar, closing said second valve thereby isolating said chamber and generating a second calibration signal which opens said first valve thereby changing the volume of said closed pneumatic system by said predetermined calibration amount.

7. A calibrated system as claimed in claim 5 wherein said means for determining and said means for generating include a controllable processor and a memory.

8. In combination with a volume plethysmograph which detects the degree of atherosclerosis, the improvement which includes a calibrated system for measuring blood volume change through an artery of a patient with a pressure cuff bound about a limb containing said artery comprising:

a controllable pneumatic pump system for establishing a plurality of discrete levels of cuff pressure in said pressure cuff as a closed pneumatic system;

a pressure sensor substantially continually sensing and generating signals representative of instantaneous cuff pressure and blood volume change through said artery at each one of said plurality of discrete levels of cuff pressure;

means for determining when a number of representative blood volume change signals are substantially similar at one of said plurality of discrete levels of cuff pressure and generating a calibration trigger signal;

means for changing a volume in said closed pneumatic system by a predetermined calibration amount based upon said calibration trigger signal;

means for generating a corrected representative blood volume signal based upon the representative instantaneous cuff pressure signal at each of said plurality of discrete levels of cuff pressure as corrected by representative instantaneous cuff pressure signal obtained substantially simultaneously with the changing of said volume by said predetermined calibration amount;

wherein said means for changing the volume by said predetermined calibration amount includes a first and a second valve and a pneumatically closed chamber with said first valve interposed between said chamber and said closed pneumatic system, said second valve in communication with said closed chamber and, when opened, providing a passage to an ambient environment, said first valve opened by said calibration trigger signal.

* * * * *